United States Patent [19]

Velenyi et al.

[11] 4,262,153

[45] Apr. 14, 1981

[54] DECOMPOSITION OF HYDROPEROXIDES USING METAL COMPLEX CATALYSTS

[75] Inventors: Louis J. Velenyi, Lyndhurst; Christos Paparizos, Cleveland; Serge R. Dolhyj, Parma, all of Ohio

[73] Assignee: The Standard Oil Company, Cleveland, Ohio

[21] Appl. No.: 973,070

[22] Filed: Dec. 26, 1978

[51] Int. Cl.³ .............................................. C07C 37/08
[52] U.S. Cl. ...................................................... 568/798
[58] Field of Search .......................................... 568/798

[56] References Cited

U.S. PATENT DOCUMENTS

| | | | |
|---|---|---|---|
| 3,928,477 | 12/1975 | Fields et al. | 568/798 |
| 4,067,912 | 1/1978 | Fields et al. | 568/798 |
| 4,075,250 | 2/1978 | Fields et al. | 568/798 |
| 4,076,759 | 2/1978 | Fields et al. | 568/798 |

*Primary Examiner*—Werren B. Lone
*Attorney, Agent, or Firm*—Gary R. Plotecher; Herbert D. Knudsen; Larry W. Evans

[57] ABSTRACT

Hydroperoxides are catalytically decomposed using a novel metal complex of the formula:

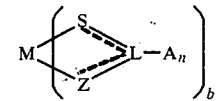

wherein
M is a positively charged metal or metal compound;
Z is S, O, P, S-P, or S-S;
L is C, P, or N; and
A is selected from the group consisting of halogens; hydrogen; N-R wherein R is selected from the group consisting of H, $C_{1-30}$ alkyls and 4 to 8 membered aryls optionally substituted with one or more $C_{1-20}$ alkyls and $C_{1-20}$ alkoxys; and hydrocarbon groups containing up to 30 carbon atoms optionally substituted with halogen atoms, $C_{1-12}$ hydroxy groups, $C_{1-12}$ acid groups, $C_{1-12}$ aldehyde groups, $C_{1-12}$ ketone groups, and $C_{1-10}$ nitrile groups; and wherein
n is 1 or 2; and
b is 1, 2 or 3.

These catalysts are especially effective in decomposing either cumene hydroperoxide or cyclohexylbenzene hydroperoxide to phenol.

23 Claims, No Drawings

DECOMPOSITION OF HYDROPEROXIDES USING METAL COMPLEX CATALYSTS

BACKGROUND OF THE INVENTION

The present invention relates to a novel process and catalyst for decomposing hydroperoxides.

The use of a metal complex catalyst to decompose hydroperoxides has been described in the prior art. For example, Japanese Pat. No. 1,138,630 discloses catalysts of the formula:

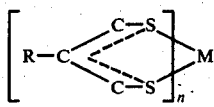

and Canadian Pat. No. 1,013,772 discloses catalysts of the formula:

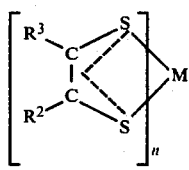

where M is a suitable metal.

However, neither of these references teach or suggest that metal complexes comprising heterocyclic rings which contain at the most one carbon atom would be effective catalysts in such processes.

Although the use of similar metal complex catalysts for the decomposition of hydroperoxides is known, there is always the desire to obtain still higher yields. Accordingly, an advantage of the instant invention is that the inventive catalysts can be used to decompose hydroperoxides at higher yields and selectivities than heretofore known.

SUMMARY OF THE INVENTION

It has now been discovered that hydroperoxides can be catalytically decomposed using a metal complex catalyst comprising a heterocyclic ring containing at the most one carbon atom. In particular, it has been discovered that phenol can be produced with high yield and selectivity by the decomposition of either cumene hydroperoxide or cyclohexylbenzene hydroperoxide using the inventive catalysts.

Thus, the present invention provides a novel process for the catalytic decomposition of hydroperoxides in which the hydroperoxide is contacted with a catalyst of the formula:

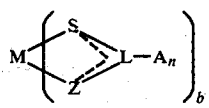

wherein
M is positively charged metal or metal compound;
Z is S, O, P, S-P, and S-S;
L is C, P, and N;
A is selected from the group consisting of halogens; hydrogen; N-R wherein R is selected from the group consisting of H, $C_{1-30}$ alkyls and 4 to 8 membered aryls optionally substituted with one or more $C_{1-20}$ alkyls and $C_{1-20}$ alkoxys; and hydrocarbon groups containing up to 30 carbon atoms optionally substituted with halogen atoms, $C_{1-12}$ hydroxy groups, $C_{1-12}$ acid groups, $C_{1-12}$ aldehyde groups, $C_{1-12}$ ketone groups, and $C_{1-10}$ nitrile groups; and
wherein
n is 1 or 2; and
b is 1, 2 or 3.

In a specific embodiment, the present invention provides a process for the liquid phase catalytic decomposition of cyclohexylbenzene hydroperoxide or cumene hydroperoxide to phenol in which the cumene hydroperoxide or cyclohexylbenzene hydroperoxide is heated in a benzene solvent in the presence of a catalyst as described below.

DETAILED DESCRIPTION

Reactants

The instant invention relates to a process for decomposing hydroperoxides. The overall reaction taking place in this process can be represented by the following equation:

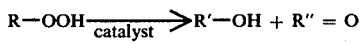

The hydroperoxide of the instant invention have the following structure:

wherein R is selected from the group consisting of:
(1) $C_{2-30}$ alkyls;
(2) monocyclic, bicyclic and tricyclic radicals in which the cyclic groups are optionally substituted with one or more halogen atom, hydroperoxides, $C_{1-30}$ alkyls, $C_{1-30}$ alkoxys, nitro groups, carboxys and carboxy esters.

Preferably, R is selected from the group consisting of:
(1) $C_{4-12}$ alkyls;
(2) phenyl optionally substituted with one or more $C_{1-4}$ alkyls; and
(3) cyclohexylbenzene radical optionally substituted with one or more $C_{1-4}$ alkyls.

Most preferably the hydroperoxide reactant is selected from the group consisting of cumene hydroperoxide and cyclohexylbenzene hydroperoxide.

Any material which is inert to the reactants, catalysts and products of the instant invention may also be included in the reaction system as a diluent. For example, inert organic materials, e.g. benzene or toluene, could be added to the reaction system if desired.

Process Conditions

The decomposition of the hydroperoxide in the presence of the catalyst proceeds very readily and can be carried out under a wide variety of reaction conditions. Preferably the reaction temperature is not permitted to reach too high a level since this could lead to the thermal decomposition of the hydroperoxide, resulting in undesired by-products. Reaction temperatures are normally maintained between 20° C. and 200° C., and more preferably between 80° C. and 120° C. Preferably, the aldehyde or ketone by-product of the instant process is continuously removed during the decomposition reaction in order to reduce the possibility of unwanted side reactions. Removal of the aldehyde or ketone may be assisted by conducting the decomposition under reduced pressure, but generally the pressure at which the decomposition is carried out is not critical and conveniently atmospheric pressure may be used.

The time required for completion of the reaction will depend on the catalyst type and temperature. The decomposition will in most cases be completed within 5 minutes to 4 hours.

In order to moderate the decomposition, the process of the present invention is generally carried out in the presence of an inert solvent, i.e. a solvent which does not react with the hydroperoxide or its decomposition products. If used, the inert solvent is preferably present in an amount such as to provide a solution containing from 1% to about 80%. Examples of inert solvents include benzene, toluene, ethylbenzene, chlorobenzene and nitrobenzene. Preferably, the inert solvent is benzene or toluene.

The decomposition may be carried out in the presence of a small quantity of water to moderate the decomposition reaction. Preferably, the amount of water added is 0.05 to 1 weight % based on the weight of the hydroperoxide.

Catalysts

The catalyst employed in the inventive process comprises a metal complex. This catalyst can be described by the formula:

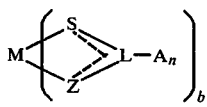

wherein
M is a positively charged metal or metal compound;
Z is selected from the group consisting of S, O, P, S-P and S-S;
L is selected from the group consisting of C, P, and N;
A is selected from the group consisting of halogens; hydrogen; N-R wherein R is selected from the group consisting of H, $C_{1-30}$ alkyls and 4 to 8 membered aryls optionally substituted with one or more $C_{1-20}$ alkyls and $C_{1-20}$ alkoxys; and hydrocarbon groups containing up to 30 carbon atoms optionally substituted with halogen atoms, $C_{1-12}$ hydroxy groups, $C_{1-12}$ acid groups, $C_{1-12}$ aldehyde groups, $C_{1-12}$ ketone groups, and $C_{1-10}$ nitrile groups; and
wherein
n is 1 or 2; and
b is 1, 2 or 3.

The catalyst may be any catalyst delineated by the general formula above with respect to the components of the catalyst. Preferred are those catalysts wherein L is C or P; Z is S-S or S; b is 2; and M is selected from the elements in Groups IB, IIB and VIII of the Periodic Table. Also preferred are those catalysts wherein A is selected from the group consisting of phenol optionally substituted with one or more $C_{1-8}$ alkyls; $C_{1-30}$ alkoxy groups; and amino groups optionally substituted with one or more $C_{1-4}$ alkyls.

The catalyst of this invention may be dissolved in the reaction medium as a homogeneous catalyst, slurried in the reaction medium as an insoluble, unsupported heterogeneous catalyst, or in some cases, where advantageous, it may be supported on carriers and slurried in the reaction medium. It is preferred, however, that the catalyst system be a homogeneous system where the catalyst is soluble in the reaction solvent.

The catalysts of the invention are prepared by known techniques. Specific preparations of these catalysts are shown in the working examples of this specification. Broadly, however, the catalysts of this invention can be prepared by any of the techniques known in the art.

The catalyst employed in the reaction is suitably employed as a dissolved component of the liquid mixture. Desirable results are obtained with the homogeneous liquid mixture because of the substantially greater contacting efficiency.

The concentration of the catalyst in the liquid phase reaction mixture may vary widely. Preferably, the catalyst concentration is 0.1 to 5 weight % based on the weight of the hydroperoxide.

Recovery

The reaction products obtained upon completion of the reaction is normally in the form of a liquid and composed primarily of alcohols, aldehydes and ketones. These reaction products can be subjected to suitable known separation techniques, e.g. solvent extraction and fractional distillation, to yield the desired end product.

For example, the liquid reaction product can be filtered to remove catalysts therefrom and then separated from any carrier gas that may be in the system. The liquid reaction product can be condensed in an alcohol or acetone trap and then separated by any suitable separation technique.

There are many known uses for the alcohols, ketones and aldehydes produced by the instant reaction. For example, products of the instant reaction may be used as monomers, solvents and intermediates for other useful compounds.

SPECIFIC EMBODIMENTS

In order to more thoroughly illustrate the present invention, the following working examples are presented. In these examples, the following definitions are used:

$$\%PPC = \frac{\text{gms. carb. in reactant conv. to prod.}}{\text{gms. carb. in reactant fed}} \times 100$$

$$\% \text{Selec} = \frac{\text{gms. carb. of reactant conv. to prod.}}{\text{gms. carb. of reactant reacted}} \times 100$$

The results have all been adjusted to a 100% carbon balance.

In general, the experimental method consisted of placing pre-weighed portions of a catalyst, solvent and hydroperoxide in a flask fed with a cold water condenser. The flask was then heated under reflux conditions for approximately 45 minutes to 1 hour. The flask was then taken from the heat, opened and the products were analyzed.

The following experiments were conducted:

EXAMPLE 1—CATALYST PREPARATION 7.314 gms. of $HN(C_2H_5)_2$ and 30 gms. of $H_2O$ were placed in a round bottom flask equipped with a condenser. 5.611 gms. of KOH, dissolved in 30 gms. of $H_2O$, were added to the flask. The flask was then placed in ice water. 11.421 gms. of $CS_2$ was slowly added and the flask was removed from the ice water and stirred for 1 hour at 60° C. 11.885 gms. of NiCl₂.6H₂O, in 50 mls. of water, were then slowly added to the solution in the flask. The resultant solution was stirred for 1 hour. After adding ether, a green precipitate formed which was separated out by filtration. The green precipitate was washed with several portions of water and dried. The green precipitate was dissolved in CH₂Cl₂ and filtered. Upon standing, fine crystals formed. The crystals were separated and dried at 110° C. The resultant catalyst can be represented by the following formula:

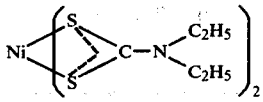

EXAMPLE 2—CATALYST PREPARATION

The procedure outlined in Example 1 was followed except that 4.607 gms. of ethanol replaced the 7.314 gms. of HN(C₂H₅)₂. The resultant catalyst is represented by the following formula:

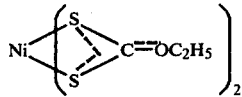

EXAMPLE 3—CATALYST PREPARATION 75 mls. of isopropylacetate (dry) was placed in a round bottom three-neck flask fitted with a condenser and thermometer. After the addition of 11.4 gms. of CS₂ the flask was cooled to 20° C. and ammonia was bubbled through with vigorous stirring. The reaction was stopped after 2½ hours. The product was extracted into 35 mls. of distilled water (bottom layer) and separated from the isopropylacetate layer. The aqueous layer was then placed in another three-necked flask, also fitted with a condenser. 11.885 gms. of NiCl₂.6H₂O and 25 mls. of water was slowly added to the aqueous layer. The resultant solution was stirred for 1 hour. The separated product was then washed and dried at 110° C. The catalyst prepared by this technique is represented by the following formula:

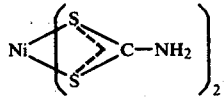

EXAMPLE 4—CATALYST PREPARATION

A Grignard reaction was started using iodobenzene and magnesium in dried ether. A small amount of this reaction mixture was added to 3.7 gms. of chlorobenzene and 0.7 gms. of magnesium in 50 ml. dried ethyl ether. 2 ml. of CS₂ was then added to this Grignard solution. After cooling, the mixture was allowed to stand overnight and then was decomposed with ice and aqueous HCl. Dithiobenzoic acid was extracted with ethyl ether and then converted to sodium dithiobenzoate by adding aqueous Na₂CO₃ to the ether extract. After removing the ether layer, 2.249 gms. of ZnCl₂ was slowly added and the mixture was stirred for one hour. The solid formed was separated, washed with water and dried. The resultant catalyst can be represented by the following formula:

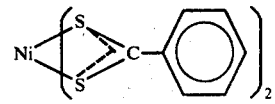

EXAMPLE 5—CATALYST PREPARATION

A mixture of 5 gms. of sulfur, 30 gms. of (NH₄)₂S and 50 mls. of tetrahydrofuran was boiled for three minutes. 65 gms. of para-isopropylbenzaldehyde was added and the reaction flask was cooled with ice water. A solution of 15 gms. of ZnCl₂ in 100 mls. of water was added with continuous stirring. The red oil formed was decanted from the upper liquid layer and washed with methanol. After further washing with 10% aqueous HCl, an orange-red precipitate was formed. The precipitate was then recrystallized with CHCl₃ and heptane. The orange-red catalyst can be represented by the following formula:

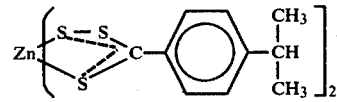

EXAMPLE 6—CATALYST PREPARATION 4 gms. of phosphorus pentasulfide was suspended in 20 cc. of benzene and heated to 75° C. to 80° C. 3.2 gms. of ethanol was added dropwise over an hour and a half while the liquid was refluxing. After the completion of the addition of the ethanol, the refluxing continued for an additional two hours. During this time the temperature of the reaction mixture rose to 95° C. to 100° C. The reaction vessel was cooled to about 4° C. by immersing it in ice water. KOH was added slowly until the solution just became alkaline. Ether was then added and a precipitate formed. The precipitate was separated and recrystallized from dioxane. 20 mls. of distilled water was then added to the recrystallized precipitate to form a solution. 4.14 gms. of NiCl₂.6H₂O in 30 mls. water was then slowly added to the solution after which the solution was stirred for one hour. The purple precipitate was filtered off from the liquid, washed with water and dissolved in chloroform. The solid formed by this procedure is a catalyst which can be represented by the following formula:

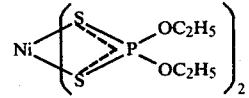

COMPARATIVE EXAMPLE A 3 gms. of NiCO₃ was dissolved in 80 mls. of 10% alcoholic HCl and cooled to approximately 0° C. in ice water. 10 mls. of acetyl acetone was then added. H₂S gas was bubbled through this mixture for 2 hours. The temperature was then increased to 60° C. and H₂S was passed through the liquid mixture for 90 minutes. The black precipitate formed was separated by filtration, washed with methanol and recrystallized from CHCl₃. The black solid catalyst formed can be represented by the following formula:

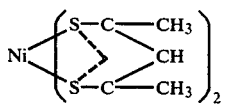

COMPARATIVE EXAMPLE B

A catalyst designated molybdenyl bis-acetylacetonate and represented by the following formula:

EXAMPLES 7-12

0.06 gms. of the catalysts produced in Examples 1 thru 6, 25 gms. of benzene and 5 gms. of cumene hydroperoxide were placed in a flask fitted with a cold water condenser. This flask was then heated to reflux for approximately 45 minutes to 1 hour. The flask was then cooled, opened and the products were analyzed. The results are shown in Table 1.

COMPARATIVE EXAMPLES C AND D

The catalysts prepared above in Comparative Examples A and B were placed in the experimental apparatus described in Examples 7-12. The results are shown in Table 1.

TABLE 1

| | | Products Obtained from Cumene HPO %ppc (Corrected) | | | | |
|---|---|---|---|---|---|---|
| Example | Catalyst | Phenol | 2-Phenyl-2-propanol | Aceto-phenone | α-methyl-styrene | Acetone | Selectivity for Phenol, % |
| 1 | Ni[(S-)₂C-N(C₂H₅)₂]₂ | 60.79 | 0.00 | 5.97 | 2.84 | 28.00 | 91.20 |
| 2 | Ni[(S-)₂C-OC₂H₅]₂ | 61.48 | 0.00 | 0.49 | 7.28 | 30.75 | 92.20 |
| 3 | Ni[(S-)₂C-NH₂]₂ | 61.32 | 0.00 | 4.23 | 3.78 | 30.66 | 92.00 |
| 4 | Zn[(S-)₂C-C₆H₅]₂ | 62.45 | 0.00 | 3.02 | 3.30 | 31.23 | 93.70 |
| 5 | Zn[(S-S)C-C₆H₄-CH(CH₃)₂]₂ | 63.98 | 0.00 | 0.00 | 4.02 | 32.00 | 96.00 |
| 6 | Ni[(S-)₂P(OC₂H₅)₂]₂ | 63.14 | 0.00 | 0.11 | 5.17 | 31.57 | 94.70 |
| A | Ni[(S-C(CH₃)=CH-C(CH₃))]₂ | 59.12 | 0.00 | 3.07 | 8.24 | 29.57 | 88.70 |
| B | O₂Mo[(O-C(CH₃)=CH-C(CH₃))]₂ | 48.22 | 3.67 | 10.04 | 13.95 | 24.12 | 72.30 |

was purchased from Climax Molybdenum Co.

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A process for decomposing a hydroperoxide comprising contacting the hydroperoxide with a catalyst of the formula:

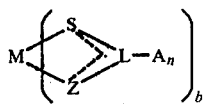

wherein
M is a positively charged metal or metal compound;
Z is S, O, P, S-P and S-S;
L is C, P and N;
A is one or more of the group consisting of halogens; hydrogen; $C_{1-30}$ alkoxy; N-$R_2$ wherein R is selected from the group consisting of H, $C_{1-30}$ alkyls and 4 to 8 membered aryls optionally substituted with one or more $C_{1-20}$ alkyls and $C_{1-20}$ alkoxys; and hydrocarbon groups containing up to 30 carbon atoms optionally substituted with halogen atoms, $C_{1-12}$ hydroxy groups, $C_{1-12}$ acid groups, $C_{1-12}$ aldehyde groups, $C_{1-12}$ ketone groups, and $C_{1-10}$ nitrile groups; and
wherein
n is 1 or 2; and
b is 1, 2 or 3;
with the proviso that when Z is S or O, then A is one or more of the group consisting of halogens; hydrogen; $NH_2$; and hydrocarbon groups containing up to 30 carbon atoms optionally substituted with halogen atoms, $C_{1-12}$ hydroxy groups, $C_{1-12}$ acid groups, $C_{1-12}$ aldehyde groups, $C_{1-12}$ ketone groups, and $C_{1-10}$ nitrile groups.

2. The process of claim 1 wherein the hydroperoxide has the following structure:

wherein R is selected from the group consisting of:
(1) $C_{2-30}$ alkyls;
(2) monocyclic, bicyclic and tricyclic radicals in which the cyclic groups are optionally substituted with one or more halogen atoms, hydroperoxides, $C_{1-30}$ alkyls, $C_{1-30}$ alkoxys, nitro groups, carboxys and carboxy esters.

3. The process of claim 2 wherein R is selected from the group consisting of:

(1) $C_{4-12}$ alkyls;
(2) phenyl optionally substituted with one or more $C_{1-4}$ alkyls; and
(3) cyclohexylbenzene optionally substituted with one or more $C_{1-4}$ alkyls.

4. The process of claim 1 wherein hydroperoxide is cumene hydroperoxide.

5. The process of claim 1 wherein the hydroperoxide is cyclohexylbenzene hydroperoxide.

6. The process of claim 1 wherein Z is S-S or S.

7. The process of claim 1 wherein n is 1.

8. The process of claim 1 wherein n is 2.

9. The process of claim 1 wherein b is 2.

10. The process of claim 1 wherein L is carbon or phosphorus.

11. The process of claim 1 wherein M is selected from the group consisting of transition metals of Groups IIB, IB and VIII.

12. The process of claim 10 wherein M is selected from the group consisting of Zn, Ni, Fe, Co, Cu and Cd.

13. The process of claim 1 wherein the decomposition is moderated by the presence of water.

14. The process of claim 1 in which the decomposition is effected at a temperature of 20° C. to 200° C.

15. The process of claim 14 in which the temperature is 80° C. to 120° C.

16. The process of claim 1 in which the decomposition is carried out in the presence of an organic solvent which is inert to the hydroperoxide, catalyst and decomposition products.

17. The process of claim 16 in which the solvent is selected from the group consisting of benzene, toluene, xylene, ethylbenzene, chlorobenzene or nitrobenzene.

18. The process of claim 1 wherein the catalyst is dissolved in the reaction medium as a homogeneous catalyst.

19. The process of claim 1 wherein the catalyst concentration is 0.1 to 5 weight % based on the weight of the hydroperoxide.

20. The process of claim 1 wherein A is selected from the group consisting of phenyl optionally substituted with one or more $C_{1-4}$ alkyls; $C_{1-30}$ alkoxys; and aminos optionally substituted with one or more $C_{1-4}$ alkyls.

21. The process of claim 1 wherein Z is selected from the group consisting of P, S-P and S-S.

22. The process of claim 1 wherein the hydroperoxide is an aromatic hydroperoxide.

23. The process of claim 1 wherein L is N.

* * * * *